United States Patent [19]

Ueda et al.

[11] Patent Number: 4,739,083

[45] Date of Patent: Apr. 19, 1988

[54] PROCESS FOR PREPARING PYRONE-3-CARBOXAMIDE COMPOUNDS

[75] Inventors: Yoichiro Ueda; Yukihisa Goto; Kazuhisa Masamoto, all of Himeji, Japan

[73] Assignee: Daicel Chemical Industries Ltd., Osaka, Japan

[21] Appl. No.: 815,919

[22] Filed: Jan. 2, 1986

[30] Foreign Application Priority Data

Jan. 10, 1985 [JP] Japan .................................. 60-2720
Jan. 29, 1985 [JP] Japan .................................. 60-15212

[51] Int. Cl.$^4$ .................. C07D 309/32; C07D 285/12; C07D 403/12
[52] U.S. Cl. .................................... 549/419; 549/414; 549/60; 548/247; 548/246; 548/245; 548/236; 548/233; 548/198; 548/195; 548/180; 548/139; 548/136; 548/128; 544/400; 544/382; 544/353; 544/310; 544/283; 544/238
[58] Field of Search ................ 549/419; 544/317, 310, 544/283, 382, 353, 400, 238; 548/128, 198, 180, 195, 139, 136, 236, 233, 247, 246, 245; 549/60, 414

[56] References Cited

U.S. PATENT DOCUMENTS 4,060,533 11/1977 Nadelson .............................. 549/419

FOREIGN PATENT DOCUMENTS 45-31663 10/1970 Japan .

OTHER PUBLICATIONS

Kato et al., Yakugakuzassi, 87 1212 (1967).
Toda et al., Chem. Pharm. Bull., 19 1477 (1971).
Kato et al., Chem. Pharm. Bull., 20 133 (1972).
Bauer et al., J. Heterocyclic Chem., 13, 291 (1976).
Dehmlow et al., Liebig Ann. Chem., 2062 (1982).
Sato et al., Chem. Pharm. Bull., 30 1315 (1982).
Yakugakuzassi, 101 40 (1981).
J. Org. Chem., 29 3548 and 3555 (1964).
J. Chem. Soc. (C), 186 (1966).

*Primary Examiner*—Nicky Chan
*Attorney, Agent, or Firm*—Stiefel, Gross & Kurland

[57] ABSTRACT

A new process for preparing a pyrone-3-carboxamide compound of the formula (IV):

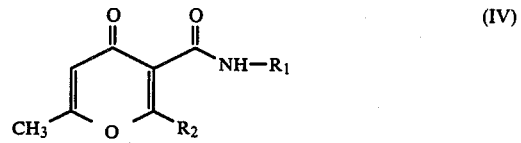

wherein $R_1$ is aryl or heterocyclic group optionally substituted, $R_2$ is alkyl, aralkyl or like group, comprising reacting a compound of the formula (I) or (I'):

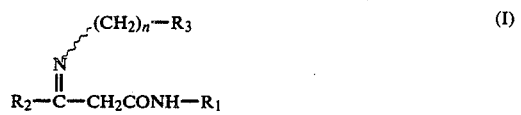

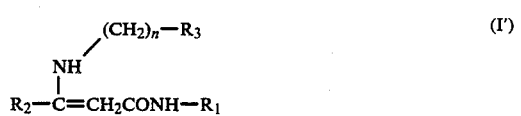

wherein $R_3$ is dialkylamino group and n is 0 to 6, and $R_1$ and $R_2$ are as above, with a compound of the formula (II):

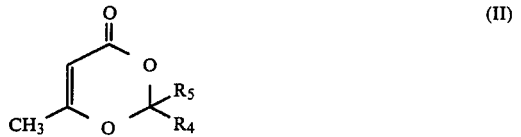

wherein $R_4$ and $R_5$ are hydrogen atom, alkyl or like group, or reacting a compound of the formula (III):

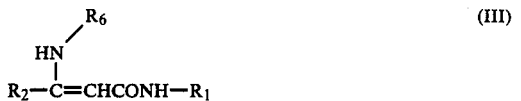

wherein $R_6$ is alkyl, aryl or like group, and $R_1$ and $R_2$ are as above, with a compound of the formula (II) or diketene in the presence of a tertiary organic base.

7 Claims, No Drawings

PROCESS FOR PREPARING PYRONE-3-CARBOXAMIDE COMPOUNDS

BACKGROUND OF THE INVENTION

1. Field of the Invention

The present invention is concerned with a new process for preparing 4-oxo-4H-pyran-3-carboxamide compounds, which are useful for medicines or pesticides, or intermediates thereof.

2. Description of the Prior Arts

There have been reported some methods for preparing 4-oxo-4H-pyran-3-carboxamide compounds concerning this invention. That is, A. Mellams et al reported that the treatment of certain acetoacetanilide derivatives with polyphosphoric acid under heating gave the corresponding 2,6-dimethyl-4-oxo-4H-pyran-3-carboxamides [cf., J. Org. Chem., 29, 3548 and 3555 (1964)]. R. Garner et al [cf., J. Chem. Soc. (c), 186(1966)] stated that Mellams et al' report was specific to certain acetoacetanilide derivatives having electron widthdrawing substituents and when acetoacetanilide itself was used in the reaction, it gave 2-hydroxyquinoline derivative but did not form the pyrone compound.

Japanese Patent Publication No. Sho 45(1970)-31,663 disclosed a method for reacting isocyanates with diketene in the presence of an acid catalyst, to yield 3,4-dihydro-2,4-dioxo-6-methyl-2H-1,3-oxazines and/or 2,6-dimethyl-4-oxo-4H-pyran-3-carboxamides (stated as 3-carbamyl-2,6-dimethyl-4-pyrones in this publication). In this reaction, the latter 2,6-dimethyl-4-oxo-4H-pyran-3-carboxamides are observed to be predominantly formed when ortho substituted compounds such as o-chlorophenylisocyanate or o-nitrophenylisocyanate, or meta substituted compounds such as m-nitrophenylisocyanate were used. This method would be effective in cases where the starting materials of isocyanates are easily available, but would be not generally applicable to any of isocyanates because reaction selectivity is largely influenced by their structure.

It has also been known that 2,6-dimethyl-4-oxo-4H-pyran-3-carboxamide compounds could be obtained by the reaction of diketene and primary arylamines, such as aniline derivatives, aminotropolones or aminopyridines.

Kato et al [cf., Yakugakuzassi, 87, 1212(1967)] reported that the reaction of diketene and aniline derivatives in the presence of a basic catalyst gave pyridone type rings, except that the use of p-nitroaniline gave 2,6-dimethyl-N-(4-nitrophenyl)-4-oxo-4H-pyran-3-carboxamide.

H. Toda et al [cf., Chem. Pharm. Bull., 19 1477(1971)] reported on the reaction between aminotropones and diketene, where the use of 4-aminotropolone and 2-aminotropone gave 4-pyrone compounds, and the use of 5-aminotropolone gave a pyridonetype ring closed compound. Kato et al [Chem. Pharm. Bull., 20 133(1972)] also reported that 2-amino- or 4-aminopyridine derivatives gave mainly 4-pyrone compounds, while 3-aminopyridine derivatives gave mainly pyridone type compounds.

The reactivity of heterocyclic amines was reported in J. Heterocyclic Chem., 13, 291(1976) by R. F. Lauer et al where 2-amino-1,3,4-thiadiazole gave a 4-pyrone compound, although its yield is unclear.

As is clear from the above statement, the reaction selectivity between diketene and primary arylamines is greatly influenced by the structure of the arylamines to be used. Therefore, it was previously impossible to predominantly yield 4-pyrone compounds as far as primary arylamines are used.

Similarly, it has been reported that the treatment of acetoacetyl derivatives of arylamines with diketene yielded either pyridone compounds or 4-pyrone compounds, depending upon the structure of said starting materials. It is especially mentioned that with N-methylaniline as a secondary arylamine it is impossible to form pyridone ring closure. This reaction gave 4-pyrone compound with approximately quantitative yield, when a quaternary ammonium chloride is used as a catalyst [cf., E. V. Dehmlow & A. R. Shamout., Liebigs Ann. Chem., 2062(1982)].

In addition, the reaction for obtaining an 4-pyrone compound from 2,2,6-trimethyl-1,3-dioxin-4-one has been known. That is, T. Kato et al [Chem, Pharm. Bull., 30, 1315(1982)] studied on the reaction between amides or acetoacetyl derivatives thereof and 2,2,6-trimethyl-1,3-dioxin-4-one and reported that the reaction of N-formylacetoacetamide with 2,2,6-trimethyl-1,3-dioxin-4-one in the presence of N,N-dimethylaniline gave a pyridone compound as the main product and 4-pyrone compound as the by-product.

The known methods for preparing 4-oxo-4H-pyran-3-carboxamide compounds as described above show as a common feature that the selectivity in reaction is influenced by the structure of the starting materials, and cannot generally apply to any of the starting materials. As a method to avoid such difficulty, Kato et al [Yakugakuzassi, 101, 40(1981)] reported that the reaction of 3-morpholinocrotonanilide derivatives and diketene under heating gave the corresponding 4-pyronecompounds, in which change in structure of 3-morpholinocroton anilide derivatives is assumed not to give any serious influence on yield. This method however yielded a mixture with pyridone compounds when 3-benzylaminocrotonanilide derivatives are used.

Thus, the present invention has been completed on the basis of observation which is different from the result predicted from the above known facts and provides a generally applicable method for preparing 4-oxo-4H-pyran-3-carboxamide compounds.

SUMMARY OF THE INVENTION

The present invention concerns a process for preparing pyrone-3-carboxamide compounds which comprises reacting a compound of the general formula (I) or (I'):

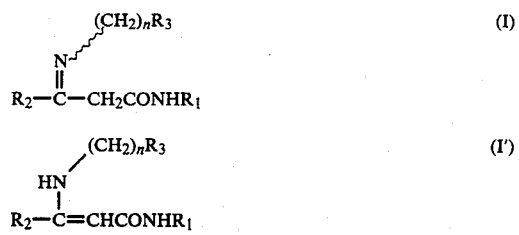

wherein $R_1$ is an aryl or heterocyclic group which may be substituted; $R_2$ is a $C_{1-11}$ alkyl, lower alkenyl, lower alkynyl, cycloalkyl, lower alkoxyalkyl, phenyl group which may be substituted, aralkyl group which may be at the nucleus substituted by one or two groups of halogen atom, lower alkyl and lower alkoxy group; halogenated alkyl or 5- or 6-membered heterocyclic group; $R_3$ is dialkylamino group and n is an integer of from 0 to 6, with a compound of the general formula (II)

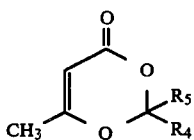

wherein $R_4$ and $R_5$ is hydrogen atom, alkyl or phenyl group or cycloalkyl group which is formed by $R_4$ and $R_5$ when both are alkyl groups, or diketene, alternatively reacting a compound of the general formula (III):

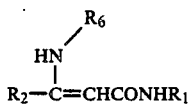

wherein $R_1$ and $R_2$ have the same meanings as in the formulae (I) and (I'), and $R_6$ is alkyl, aralkyl, cycloalkyl, aryl or heterocyclic group, with a compound of the formula (II) or diketene in the presence of a tertiary organic base, to obtain a compound of the general formula (IV):

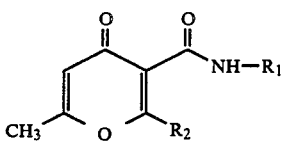

wherein $R_1$ and $R_2$ have the same meanings as in the formulae (I) and (I').

The compounds of the general formulae (I), (I') and (III) may be obtained by condensing a β-ketoamide derivative of the general formula (V):

$R_2-COCH_2CONHR_1$     (V), wherein $R_1$ and $R_2$ are the same as in the general formulae (I), (I') and (III), with a primary amine of the general formula (VI) or (VII):

$H_2N(CH_2)_nR_3$     (VI)

$H_2NR_6$     (VII), wherein $R_3$, $R_6$ and n are the same as in the general formulae (I), (I') and (III). The general formulae (I) and (I') mean the tautomers of compounds which can exchange to each others and their ratio is different by n and $R_1$ in the formulae.

$R_1$ in the general formulae (I), (I'), (III) and (IV) is an aryl or heterocyclic group which may be substituted. Examples of aryl groups include phenyl and naphthyl and heterocyclic groups including 5- or 6-membered heterocyclic ones having one to three hetero atoms selected from nitrogen, sulphur and oxygen atoms, specifically 5-membered ring group such as furyl, tetrahydrofuryl, thienyl, thiazolyl, isothiazolyl, oxazolyl, isooxazolyl or pyrazol group; and 6-membered ring group such as pyridyl, pyrimidinyl, pyrazinyl or pyridazinyl.

The substituents for such groups are not limited, if they are inert in the reaction. Concrete examples are a halogen atom such as chlorine, bromine or fluorine atom; alkyl group such as methyl, ethyl, propyl, isopropyl or butyl group; alkoxy group such as methoxy, ethoxy or propoxy group; alkoxycarbonyl such as methoxycarbonyl or ethoxycarbonyl; cyano group, nitro group and trifluoromethyl group. The aryl group or heterocyclic group may be substituted by one to three groups, preferably one to two groups of the above mentioned substituents.

As discussed above, the $R_1$ group is desirably selected from the standpoint of the utility of the end products as pesticides such as plant growth inhibitory agent, or medicine such as anti-inflammatory agent, although the characteristic of the present invention exists in the reaction itself.

$R_2$ group in the general formulae (I), (I'), (III) and (V) is a $C_{1-11}$ alkyl, lower alkenyl, lower alkynyl, cycloalkyl, lower alkoxyalkyl group; phenyl group which may be substituted; an aralkyl group which may be at the nucleus substituted by one to two groups of halogen, lower alkyl or alkoxy group; halogenated alkyl group or 5- or 6-membered heterocyclic group. Examples of lower alkenyl and alkynyl groups include vinyl, allyl, isopropenyl, 2-butenyl, 1,3-butadienyl, 2-pentenyl, 1,4-pentadienyl, 1,6-heptadienyl, 1-hexenyl, ethynyl, 2-propenyl and the like.

Examples of cycloalkyl groups include cyclopropyl, cyclopentyl, cyclohexyl and the like.

Examples of halogenated alkyl groups include trifluoromethyl, chloromethyl and the like.

The lower alkoxyalkyl group includes methoxymethyl, ethoxymethyl, propoxymethyl, butoxymethyl and the like.

The halogen atom includes chlorine, bromine, iodine and fluorine atom.

Lower alkyl group includes methyl, ethyl, propyl, isopropyl, butyl, isobutyl, pentyl and isopentyl.

Lower alkoxy group includes methoxy, ethoxy, propoxy, isopropoxy and butoxy.

Aralkyl group includes benzyl, 3-phenylpropyl, 4-phenylbutyl and the like.

5- or 6-membered heterocyclic group includes a 5- or 6-membered one containing 1-3 hetero atoms selected from nitrogen, oxygen and sulfur. Examples of the 5-membered heterocyclic groups include furyl, tetrahydrofuryl, thienyl, thiazolyl, isothiazolyl, oxazolyl, isooxazolyl and pyrazolyl, and examples of the 6-membered heterocyclic groups include pyridyl, pyrimidinyl, pyrazinyl and pyridazinyl. These heterocyclic groups may be substituted by alkyl such as methyl or ethyl, halogen atom or phenyl radical. When the heterocyclic group is substituted by phenyl, it may form a condensed ring combining the two adjacent carbon atoms in the heterocyclic group with the phenyl group. Examples of the condensed rings include benzothiazolyl, benzofuryl, quinazolinyl and quinoxalinyl.

$R_3$ is a dialkylamino group in which the alkyl group means methyl, ethyl, propyl, isopropyl, butyl and the like, and both of the alkyl groups may form cycloalkyl group such as cyclopropyl, cyclopentyl, cyclohexyl and the like, and also may form a heterocyclic ring with nitrogen atom of amino group to which the alkyl groups are bonded and other hetero atom according to circumstances. Examples of heterocyclic rings include pyrrolidine, piperidine, piperazine, morpholine and the like.

In the general formulae (I) and (I'), n is an integer from 0 to 6. When n is zero, the formula (I) or (I') means a compound having hydrazino linkage.

The primary amine compound of the formula (VI) which is the raw material for the preparation of the compound of the formula (I) or (I') includes N,N-dimethyl hydrazine, N,N-diethyl hydrazine, N-aminopyrrolidine, N-aminopiperidine, N-aminomorpholine, 1-amino-4-methylpiperazine, N,N-dimethyl ethylenediamine, N,N-diethylethylenediamine, N-(2-aminoethyl)pyrrolidine, N-(2-aminoethyl)piperidine, N-(2-aminoethyl)morpholine, N-(3-aminopropyl)morpholine, N-(6-aminohexyl)morpholine and the like.

On the other side, the reactant for the compound of the formula (I), (I') or (III) is diketene or 6-methyl-4H-1,3-dioxin-4-one of the general formula (II). The latter compound is an addition product of diketene with a ketone or an aldehyde and can be prepared by the conventional known methods [cf., M. F. Carrol & A. R. Bader, J. Amer. Chem. Soc., 74 6305(1952); ibid., 75 5400(1953); E. V. Dehmlow & A. R. Shamout, Liebigs Ann. Chem., 1753(1982)]

$R_4$ and $R_5$ in the general formula (II) are hydrogen atom, alkyl or phenyl group and when both of $R_4$ and $R_5$ are alkyl groups, they may be combined to form cycloalkyl group. Since these $R_4$ and $R_5$ groups do not remain in the object compounds, they are desirably selected from groups which are easily available with cheap cost. A preferable compound of the formula (II) is 2,2,6-trimethyl-4H-1,3-dioxin-4-one.

In $R_6$ of the formula (III), alkyl group includes $C_1$-$C_{11}$ alkyl; aralkyl group includes benzyl, 2-phenylethyl, etc.; cycloalkyl group includes ones having 3-7 carbon atoms, and aryl or heterocyclic group which may be substituted includes the same as examples of those in $R_1$.

Examples of tertiary organic bases are aliphatic and aromatic tertiary amines, and nitrogen-containing heterocyclic bases. Examples of tertiary aliphatic amines are triethylamine, tripropylamine, triisobutylamine, N,N-dimethylbenzylamine, N,N-dimethylcyclohexylamine, N,N,N',N'-tetramethylethylenediamine, N,N,N',N'-tetramethyl-1,3-propanediamine.

Examples of aromatic tertiary amines are N,N-dimethyl aniline, N,N-diethylaniline, N,N-dimethyl-o-toluidine. Examples of nitrogen-containing heterocyclic bases are N-methylpyrrolidine, N-methylpiperidine, N,N'-dimethylpiperazine, N-methylmorpholine and 1,4-diazabicyclo[2,2,2]octane.

In this invention, the reaction of the compound of the formula (II) may be conducted in the absence of solvent, but more preferably be conducted in the presence of an aromatic hydrocarbon as the reaction solvent, such as benzene, toluene or xylene to make a homogeneous state.

The reaction temperature is desirably in the range from 100° C. to 150° C., taking into consideration a thermal decomposition temperature of the compound of the formula (II) to be employed. From the view point of the reaction rate, the temperature is preferably at 110°-140° C.

The amount of the compound of the formula (II) is equivalent to or greater than the amount of the compound of the formula (I), (I') or (III) and preferably is at a molar ratio of 1.5-3.0 to achieve a good result.

When the compound of the formula (II) is used, a carbonyl compound of the formula (VIII) is formed as a thermally decomposed product in the course of the reaction.

If the boiling point of this carbonyl compound is lower than the set-up reaction temperature, the reaction is advantageously carried out while distilling it off together with a portion of the solvent employed. Accordingly, it is preferable to conduct the reaction at the reflux temperature of the solvent used.

On the other side, when diketene is used as the reactant, the reaction is preferably conducted in a homogeneous state with an aromatic hydrocarbon as the reaction solvent, such as benzene, toluene or xylene; at a temperature up to 130° C. The upper limit of the reaction temperature is limited to a boiling point of diketene, excepting that the reaction is conducted under pressure. Diketene is used in an amount equivalent to or greater than the amount of the compound of formula (I), (I') or (III), preferably 1.5-3.0 moles to one mole of the compound of the formula (I), (I'), or (III), in order to achieve a good result.

In the reaction of the compound of the formula (III) with diketene or the compound of the formula (II), the tertiary organic base is used at a ratio of 0.5 or more moles, preferably one or more moles, to one mole of the compound of the formula (III).

The use of a molar ratio of 10 or more of the tertiary organic base will not provide any further effect. The tertiary organic base is selected from the above mentioned examples, but preferably is tiethylamine, N,N,N',N'-tetramethylethylenediamine, N,N'-dimethylaniline or N-methylpiperidine.

According to the method of this invention, 4-oxo-4H-pyran-3-carboxamide compounds which could not be selectively prepared may be obtained in a good yield by use of easily available raw materials and compact procedures.

This invention is further illustrated by the following examples.

EXAMPLE 1

N-(2,6-diethylphenyl)-2,6-dimethyl-4-oxo-4H-pyran-3-carboxamide

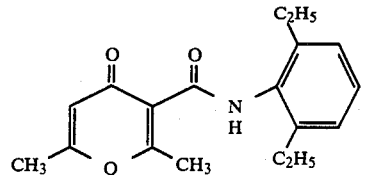

A mixture of 23.3 g (100 m mol) of 2,6-diethylacetoacetanilide, 12.0 g (200 m mol) of N,N-dimethylhydrazine and 125 ml of toluene was stirred for 8 hours at 60° C. The reaction mixture was heated, unreacted N,N-dimethylhydrazine was distilled off, and the resulted water was removed from the reaction system and the system was then dried to remove the solvent with rotary-evaporator under reduced pressure. A solid residue was obtained and was recrystallized with hexane in usual way. 25.6 g of N-(2,6-diethylphenyl)-3-(N,N-dimethylhydrazono)butyramide was obtained as colorless clear crystals (m.p.: 107°-108.5° C.)

Yield: 93%).

I.R. spectrum (KBr disc): νc=0 1642 cm⁻¹.

NMR δ-value (CDCl₃): 1.16 (t, 6H), 2.10 (s, 3H), 2.48 (s, 6H), 2.55 (q, 4H), 3.33 (s) and 3.52 (s) integration ratio 1:1 (sum up 2H), 6.85-7.35 (m, 3H), 8.20-9.10 (1H).

A mixture of 25.0 g (90.8 m mol) of N-(2,6-diethylphenyl)-3-(N,N-dimethylhydrazono)butyramide and 130 ml of toluene was refluxed, to which a solution of 28.4 g (200 m mol) of 2,2,6-trimethyl-4H-1,3-dioxin-4-one was dropwise added over a period of 30 minutes. The mixture was further refluxed for 2 hours. After distilling off the solvent, 200 ml of ethyl ether was added to the residue. The mixture was well stirred and filtered to remove insoluble material. The filtrate was concentrated and subjected to chromatography to remove high polar impurities. The resultant product was recrystallized from hexane to obtain 20.2 g (Yield 74%) of the title compound.

m.p.: 83.5°-84.5° C.

I.R. spectrum (KBr disc): νc=0 1655, 1675 cm⁻¹.

NMR δ-value (CDCl₃): 1.17 (t, 6H), 2.29 (s, 3H), 2.61 (q, 4H), 2.80 (s, 3H), 6.24 (s, 1H), 7.08 (s, 3H), 11.0 (br., 1H).

EXAMPLE 2

2,6-Dimethyl-N-(2,3-dimethylphenyl)-4-oxo-4H-pyran-3-carboxamide

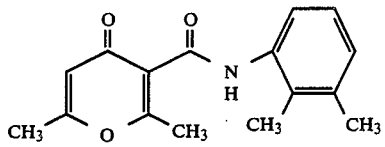

A mixture of 10.3 g (50 m mol) of N-(2,3-dimethylphenyl)-3-oxo-butyramide, 4.50 g (75 m mol) of N,N-dimethylhydrazine and 60 ml of toluene was stirred for 8 hours at 60° C.

Then, unreacted N,N-dimethylhydrazine and the resulted water together with about 10 ml of toluene were distilled off from the reaction system. 10.5 g (125 m mol) of diketene was dropwise added to the remaining solution over a period of 5 minutes, while refluxing. The mixture was further refluxed for 2 hours and was cooled to room temperature. The resulting crystals were filtered off, washed and dried to obtain 8.63 g (Yield 64%) of the title compound.

m.p.: 174.5°-175.5° C.

I.R. spectrum (KBr disc): νc=0 1645, 1675 cm⁻¹.

NMR δ-value (CDCl₃): 2.28 (s, 9H), 2.83 (s, 3H) 6.23 (s, 1H), 6.70-8.00 (m, 3H) 11.66 (br., 1H).

EXAMPLE 3

N-2,6-dimethoxypyrimidine-4-yl)-2,6-dimethyl-4-oxo-4H-pyran-3-carboxamide

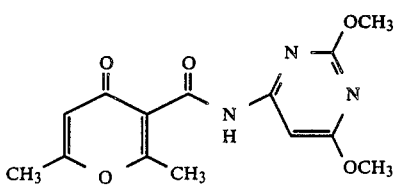

A mixture of 4.78 g (20 m mol) of N-(2,6-dimethoxypyrimidine-4-yl)-3-oxo-butyramide (m.p. 107°-109° C.), 1.20 g (20 m mol) of N,N-dimethylhydrazine and 30 ml of toluene was, after adding one drop of acetic acid, stirred for 2 hours at 80° C.

Then, unreacted N,N-dimethylhydrazine and the resulted water together with about 10 ml of toluene were distilled off from the reaction system. 3.40 g (40 m mol) of diketene was added to the remaining solution while refluxing. The mixture was further refluxed for 2 hours and was cooled to room temperature. The resulting crystals were filtered off, washed and dried to obtain 5.87 g (Yield 96%) of the title compound.

m.p.: 202°-230.5° C.

I.R. spectrum (KBr disc): νc=0 1653, 1700 cm⁻¹.

NMR δ-value (CDCl₃): 2,28 (s, 3H), 2.78 (s, 3H) 3.91 (s, 6H), 6.20 (s, 1H) 7.17 (s, 1H), 12.25 (br., 1H).

EXAMPLE 4

2,6-Dimethyl-N-(5-methyl-1,3,4-thiadiazole-2-yl)-4-oxo-4H-pyran-3-carboxamide

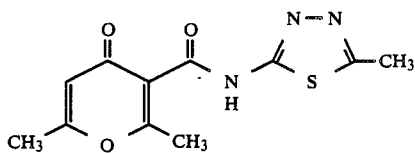

The title compound was prepared from N-(5-methyl-1,3,4-thiadiazole-2-yl)-3-oxo-butyramide (m.p. 181°-182° C.) as the raw material in the similar way to the method described in Example 3.

(Yield: 58%)

m.p.: 203°-204° C.

I.R. spectrum (KBr disc): νc=0 1655, 1690 cm⁻¹.

NMR δ-value (CDCl₃): 2.33 (s, 3H), 2.68 (s, 3H) 2.85 (s, 3H), 6.27 (s, 1H) 12.50-14.50 (br., 1H).

EXAMPLE 5

N-(2-chlorophenyl)-2,6-dimethyl-4-oxo-4H-pyran-3-carboxamide

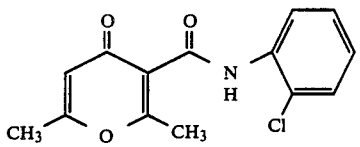

A mixture of 4.23 g (20 m mol) of o-chloroacetoacetanilide, 2.28 g (20 m mol) of 1-(2-aminoethyl)-pyrrolidine and 20 ml of toluene was, after adding one drop of acetic acid, stirred for 1 hour at 80° C. and further refluxed 1 hour. After distilling off the resulting water together with about 10 ml of toluene, a solution of 7.81 g (50 m mol) of 2-ethyl-2,6-dimethyl-4H-1,3-dioxin-4-one in 25 ml of toluene was dropwise added to the remaining solution over a period of 15 minutes while refluxing. The reaction solution was further refluxed for 2.5 hours while distilling off about 12 ml of toluene and was cooled to room temperature. The resulting crystals were filtered off, washed and dried under reduced pressure to obtain 4.53 g (Yield 82%) of the title compound.

m.p.: 206°-207° C.

I.R. spectrum (KBr disc): νc=0 1650, 1695 cm⁻¹.

NMR δ-value (CDCl₃): 2.28 (s, 3H), 2.83 (s, 3H), 6.24 (s, 1H), 6.70-8.60 (m, 4H), 12.42 (br., 1H).

EXAMPLE 6

2,6-Dimethyl-4-oxo-N-phenyl-4H-pyran-3-carboxamide

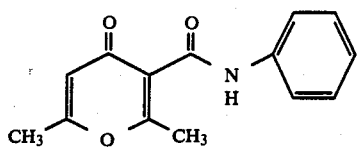

A mixture of 3.54 g (20 m mol) of acetoacetanilide, 1.76 g (20 m mol) of N,N-dimethylethylenediamine and 20 ml of toluene was, after adding one drop of acetic acid, stirred for 1 hour at 80° C. and was refluxed for 1 hour while distilling off the resulted water with about 12 ml of toluene.

A solution of 7.10 g (50 m mol) of 2,2,6-trimethyl-4H-1,3-dioxine-4-one in 25 ml of toluene was dropewise added to the remaining solution over a period of 30 minutes while refluxing. The reaction solution was further refluxed for 1 hour while distilling off about 12 ml of toluene and was cooled to room temperature. The resulting crystals were filtered, washed and dried under reduced pressure to obtain 2.51 g (Yield 52%) of the title compound.

m.p.: 148.5°–149° C.

I.R. spectrum (KBr disc): $vc=0$ 1652, 1682 $cm^{-1}$.

NMR δ-value (CDCl$_3$): 2.24 (s, 3H), 2.82 (s, 3H) (6.20 (s, 1H), 6.80–7.80 (m, 5H) 11.97 (br., 1H).

EXAMPLE 7-13

β-Ketoamide derivatives corresponding to the object compounds were used and reacted in a similar way to the method described in Example 2 and the following compounds were obtained.

N-(4-chlorophenyl)-2,6-dimethyl-4-oxo-4H-pyran-3-carboxamide (Example 7).
N-(2,6-dichlorophenyl)-2,6-dimethyl-4-oxo-4H-pyran-3-carboxamide (Example 8).
N-(2-chloro-6-methylphenyl)-2,6-dimethyl-4-oxo-4H-pyran-3-carboxamide (Example 9).
2,6-dimethyl-N-(2-methylphenyl)-4-oxo-4H-pyran-3-carboxamide (Example 10).
2,6-dimethyl-N-(2,6-dimethylphenyl)-4-oxo-4H-pyran-3-carboxamide (Example 11).
N-(2-ethyl-6-methylphenyl)-2,6-dimethyl-4-oxo-4H-pyran-3-carboxamide (Example 12).
2-ethyl-6-methyl-4-oxo-N-phenyl-4H-pyran-3-carboxamide (Example 13).

The physical properties of these compounds are given in Table 1.

EXAMPLE 14

6-Methyl-4-oxo-N,2-diphenyl-4H-pyran-3-carboxamide

The title compound was prepared from α-benzoylacetoanilide as the raw material in a similar way to the method described in Example 6. (Yield: 43%)

m.p.: 222°–226° C.

I.R. spectrum (KBr disc): 1607, 1655, 1675 $cm^{-1}$.

NMR δ-value (DMSO.d$^6$): 2.36 (s, 3H), 6.28 (s, 1H), 6.80–7.80 (m, 10H), 10.23 (1H, br).

EXAMPLE 15

6-Methyl-4-oxo-N-phenyl-2-propyl-4H-pyran-3-carboxamide. A mixture of 2.05 g (10 m mol) of 3-oxo-N-phenylhexanamide (m.p. 77.0°–78.5° C.), 0.9 g (15 m mol) of N,N-dimethylhydrazine and 15 ml of toluene was stirred for 8 hours at 60° C. Then, unreacted N,N-dimethylhydrazine and the resulted water, together with about 2 ml of toluene were distilled off outside the reaction system. A solution of 3.90 g (25 m mol) of 2-ethyl-2,6-dimethyl-4H-1,3-dioxin-4-one in 8 ml of toluene was dropwise added to the remaining solution over a period of 30 minutes, while refluxing. The mixture was further refluxed for 2.5 hours and 3 ml of toluene was distilled off outside the reaction system. The reaction mixture was cooled to room temperature. The resulted crystals were filtered off, washed and dried to obtain 1.32 g (Yield: 49%) of the title compound.

m.p.: 133.0°–134.0° C.

I.R. spectrum (KBr disc): $vc=0$ 1657, 1697 $cm^{-1}$.

NMR δ-value (CDCl$_3$): 1.02 (t, 3H), 1.75 (six, 2H) 2.38 (s, 3H), 6.18 (s, 1H) 6.90–7.70 (m, 5H), 11.92 (br., 1H).

TABLE 1

| Example No. | Yield (%) | m.p. (°C.) | IR(KBr disc) $vc = 0\ (cm^{-1})$ | NMR(CDCl$_3$) δ-value |
|---|---|---|---|---|
| 7 | 67 | 194–197 | 1650,1688 | 2.27(s,3H), 2.81(s,3H), 6.20(s,1H), 7.00–7.80(m,4H), 12.05(br.,1H). |
| 8 | 44 | 188–189.5 | 1650,1680 | 2.31(s,3H), 2.82(2,3H), 6.27(s,1H), 6.90–7.50(m,3H), 11.70(br.,1H). |
| 9 | 45 | 145–148 | 1655,1678 | 2.28(s,6H), 2.80(s,3H), 6.24(s,1H), 6.70–7.50(m,3H), 11.40(br.,1H). |
| 10 | 63 | 165–166 | 1652,1690 | 2.26(s,3H), 2.87(s,3H), 2.84(s,3H), 6.20(s,1H), 6.75–8.25(m,4H), 11.80(br.,1H). |
| 11 | 63 | 111.5–112 | 1650,1678 | 2.28(s,6H), 2.79(s,3H), 6.22(s,1H) 7.00(s,3H), 11.18(br.,1H). |
| 12 | 58 | 57–58.5 | 1653,1683 | 1.18(t,3H), 2.24(s,3H), 2.28(s,3H), 2.68(q,2H), 2.80(s,3H), 6.28(s,1H), 7.04(s,3H), 10.97(br.,1H) |
| 13 | 35 | 154.5–156 | 1650,1700 | 1.31(t,3H), 2.27(s,3H), 3.28(q,2H), 6.18(s,1H) 6.90–7.70(m,5H), 11.90(br,1H) |

EXAMPLE 16

2-Ethyl-6-methyl-4-oxo-N-phenyl-4H-pyran-3-carboxamide

The title compound was prepared from 3-oxo-N-phenylvaleramide (m.p. 84.0°–85.5° C.) and 2,2,6-trimethyl-4H-1,3-dioxin-4-one, instead of 2-ethyl-2,6-dimethyl-4H-1,3-dioxin-4-one in Example 15, as the raw materials in a similar way to the method described in Example 15. (Yield: 49%) m.p.: 154.5°–156° C.

I.R. spectrum (KBr disc): $v=0$ 1650, 1700 $cm^{-1}$.

NMR δ-value (CDCl$_3$): 1.31 (t, 3H), 2.27 (s, 3H), 3.28 (q, 2H), 6.18 (s, 1H), 6.90–7.70 (m, 5H), 11.90 (br., 1H).

EXAMPLE 17

6-Methyl-N-(2,3-dimethylphenyl)-4-oxo-2-propyl-4H-pyran-3-carboxamide

The title compound was prepared from N-(2,3-dimethylphenyl)-3-oxo-hexanamide (m.p. 59.5°–60.5° C.) as raw material in a similar way to the method described in Example 15. (Yield: 51%)

m.p.: 133°–135° C.

I.R. spectrum (KBr disc): 1620, 1660, 1695 cm$^{-1}$.

NMR δ-value (CDCl$_3$): 1.02 (t, 3H), 1.68 (six, 2H), 2.25 (s, 3H), 2.29 (s, 6H), 3.26 (t, 2H), 6.21 (s, 1H), 6.85–7.80 (m, 3H), 11.60 (br., 1H).

EXAMPLE 18–21

β-Ketoamide derivatives corresponding to object compounds were reacted in a similar way to the method discribed in Example 5, except that 2-ethyl-2,6-dimethyl-4H-1,3-dioxin 4-one was replaced by 2,2,6-trimethyl-4H-1,3-dioxin and the following object compounds were obtained.

2-ethyl-6-methyl-4-oxo-N-phenyl-4H-pyran-3-carboxamide (Yield: 73%) (Example 18)

N-(2-chlorophenyl)-6-methyl-4-oxo-2-phenyl-4H-pyran-3-carboxamide (Yield: 27%) (Example 19)

m.p.: 168°–170° C.

I.R. spectrum (KBr disc): $vc=0$ 1655, 1700 cm$^{-1}$.

NMR δvalue (CDCl$_3$): 2.34 (s, 3H), 6.31 (s, 1H), 6.80–8.32 (m, 9H), 10.23 (br., 1H).

6-Methyl-N-(2,3-dimethylphenyl)-4-oxo-2-phenyl-4H-pyran-3-carboxamide (Yield: 40%) (Example 20).

m.p.: 164°–166° C.

I.R. spectrum (KBr disc): $vc=0$ 1655, 1697 cm$^{-1}$.

NMR δ-value (CDCl$_3$): 2.24 (s, 6H), 2.31 (s, 3H) 6.23 (s, 1H), 6.70–7.65 (m, 8H) 10.47 (br., 1H).

6-Methyl-4-oxo-N,2-diphenyl-4H-pyran-3-carboxamide (Yield: 68%) (Example 21).

EXAMPLE 22

N-(2,6-diethylphenyl)-6-methyl-4-oxo-2-phenyl-4H-pyran-3-carboxamide

The title compound was prepared from N-(2,6-diethylphenyl)-3-oxo-3-phenylpropionamide as raw material in a similar way to the method described in Example 18–21. After the reaction, the resulting solution was concentrated to obtain a residue. The residue was subjected to column chromatography and the object compound was obtained (Yield: 41%).

m.p.: 186°–189° C.

I.R. spectrum (KBr disc): 1603, 1623, 1647, 1663 cm$^{-1}$.

NMR δ-value (CDCl$_3$): 1.16 (t, 6H), 2.32 (s, 3H), 2.58 (q, 4H), 6.27 (s, 1H), 7.00–7.50 (m, 8H), 9.87 (br., 1H).

EXAMPLE 23

6-Methyl-4-oxo-2-pentyl-N-phenyl-4H-pyran-3-carboxamide

The title compound was prepared from 3-oxo-N-phenyloctanamide (m.p.: 83.0°–84.0° C.) in a similar way to the method described in Example 15. After the reaction, the reaction solution was moved into a separating funnel and washed with 6NHCl. After washing with water, the organic phase was separated, dried and concentrated. The crystalline residue was recrystallized from a mixture of ethyl acetate and hexane to obtain the title compound (Yield: 50%).

m.p.: 93.5°–94.5° C.

I.R. spectrum (KBr disc): $vc=0$ 1655, 1705 cm$^{-1}$.

NMR δ-value (CDCl$_3$): 0.70–2.00 (m, 9H), 2.24 (s, 3H), 3.20 (t, 2H), 6.16 (s, 1H), 6.90–7.70 (m, 5H), 11.86 (br., 1H).

EXAMPLE 24, 25

The following compounds were obtained in a way similar to the method described in Example 23, except that 3-oxo-N-phenyloctanamide was replaced by β-ketoamide corresponding to the object compounds.

2-Butyl-6-methyl-4-oxo-N-phenyl-4H-pyran-3-carboxamide (Yield: 43%) (Example 24).

m.p.: 99.5°–101.0° C.

I.R. spectrum (KBr disc): $vc=0$ 1657, 1707 cm$^{-1}$.

NMR δ-value (CDCl$_3$): 0.70–2.00 (m, 7H), 2.28 (s, 3H), 3.27 (t, 2H), 6.19 (s, 1H), 6.90–7.70 (m, 5H), 11.90 (br., 1H).

6-Methyl-N-(2-methylphenyl)-4-oxo-2-propyl-4H-pyran-3-carboxamide (Yield: 45%) (Example 25).

m.p.: 118.5°–120.5° C.

I.R. spectrum (KBr disc): 1620, 1657, 1697 cm$^{-1}$.

NMR δ-value (CDCl$_3$): 1.00 (t, 3H), 1.75 (six, 2H), 2.28 (s, 3H), 2.36 (s, 3H), 3.23 (t, 2H), 6.16 (s, 1H), 6.80–8.10 (m, 4H), 11.76 (br., 1H).

EXAMPLE 26

N-(2-chlorophenyl)-2,6-dimethyl-4-oxo-4H-pyran-3-carboxamide

A mixture of 4.23 g (20 m mol) of o-chloroacetoacetanilide, 1.46 g (20 m mol) of butylamine and 20 ml of toluene, after adding one drop of acetic acid, was stirred for 1.5 hours at 60° C. and was refluxed for 30 minutes while distilling off the resulted water together with about 10 ml of toluene from the reaction system. After adding 4.65 g (40 m mol) of N,N,N',N'-tetramethylethylenediamine, a solution of 7.10 g (50 m mol) of 2,2,6-trimethyl-4H-1,3-dioxin 18 ml of toluene was dropwise added to the remaining solution over a period of 30 minutes while refluxing. The mixture was further refluxed for 1.5 hours. From the reaction mixture, about 12 ml of solvent was distilled off from the reaction system and then the reaction mixture was cooled to room temperature. The resulting crystals were filtered off, washed and dried under reduced pressure to obtain 4.50 g (Yield: 73%) of the title compound.

m.p.: 206°–207° C., [m.p. of this compound was reported as 201°–204° C. in J. Org. Chem., 29 3555(1964)].

I.R. (KBr disc): $vc=0$ 1650, 1695 cm$^{-1}$.

NMR δvalue (CDCl$_3$): 2.28 (s, 3H), 2.83 (s, 3H) 6.24 (s, 1H), 6.70–8.60 (m, 4H) 12,42 (br., 1H).

EXAMPLE 27

2,6-Dimethyl-N-(2-methylphenyl)-4-oxo-4H-pyran-3-carboxamide

A mixture of 3.82 g (20 m mol) of o-methylacetoacetanilide, 1.46 g (20 m mol) of butylamine and 20 ml of toluene, after adding one drop of acetic acid, was stirred for 1.5 hours at 60° C. and was refluxed for 30 minutes while distilling off the resulted water together with about 10 ml of toluene. After adding 9.30 g (80 m mol) of N,N,N',N'-tetramethylethylenediamine, a solution of 7.10 g (50 m mol) of 2,2,6-trimethyl-4H-1,3-dioxin-4-one in 18 ml of toluene was dropwise added to the remaining solution over a period of 30 minutes while refluxing. The mixture was further refluxed for 1.5 hours. After distilling off about 12 ml of solvent, the reaction mixture was spontaneouly cooled to the room temperature. The resulting crystals were filtered off, washed and dried under reduced pressure to obtain 2.63 g (Yield: 51%) of the title compound.

m.p.: 165°-166° C. [m.p. of the compound was reported as 159° C. in Japanese Patent Publication Sho 45(1970)-31663].

I.R. (KBr disc): $\nu c=0$ 1652, 1690 cm$^{-1}$.

NMR δvalue (CDCl$_3$): 2.26 (s, 3H), 2.37 (s, 3H), 2.84 (s, 3H), 6.20 (s, 1H), 6.75-8.25 (m, 4H), 11.80 (br., 1H).

EXAMPLE 28

2,6-Dimethyl-N-(4-nitrophenyl)-4-oxo-4H-pyran-3-carboxamide 4.95 g (Yield 86%) of the title compound was obtained in a similar way to the method described in Example 27, except that p-nitroacetoacetanilide was used as raw material.

m.p.: 229°-231° C. [The m.p. of the title compound was reported 223°-225° C. in Yakugakuzassi 87 1212(1967)].

EXAMPLE 29

2,6-Dimethyl-N-(2,3-dimethylphenyl)-4-oxo-4H-pyran-3-carboxamide 1.94 g (Yield 36%) of the title compound was obtained in a similar way to the method in Example 26, except that N-(2,3-dimethylphenyl)-3-oxo-butyramide was used as raw material.

m.p.: 174.5°-175.5° C.

I.R. (KBr disc): $\nu c=0$ 1645, 1675 cm$^{-1}$.

NMR δvalue (CDCl$_3$): 2.28 (s, 9H), 2.83 (s, 3H), 6.23 (s, 1H), 6.70-8.00 (m, 3H), 11.66 (br., 1H).

EXAMPLE 30

2,6-Dimethyl-4-oxo-N-phenyl-4H-pyran-3-carboxamide

A mixture of 3.54 g (20 m mol) of acetoacetanilide, 1.46 g (20 m mol) of butylamine and 20 ml of toluene, after adding one drop of acetic acid, was stirred for 1.5 hours at 60° C. and was refluxed for 30 minutes while distilling off the resulted water together with about 10 ml of toluene. After adding 12.14 g (120 m mol) of triethylamine, a solution of 7.10 g (50 m mol) of 2,2,6-trimethyl-4H-1,3-dioxin-4-one in 18 ml of toluene was dropwise added over a period of 30 minutes and the reaction mixture was further refluxed for 20 minutes. About 12 ml of solvent was distilled off from the reaction system. The reaction mixture was cooled to room temperature and the resulting crystals were filtered off, washed and dried under reduced pressure to obtain 1.58 g (Yield 33%) of the title compound.

m.p.: 148°-149° C. [The m.p. of this compound was reported as 143° C. in Japanese Patent Publication Sho 45(1970)-31663].

I.R. (KBr disc): $\nu c=0$ 1652, 1682 cm$^{-1}$.

NMR δvalue (CDCl$_3$): 2.24 (s, 3H), 2.82 (s, 3H), 6.20 (s, 1H), 6.80-7.80 (m, 5H), 11.97 (br., 1H).

EXAMPLE 31

N-(2,6-dimethoxypyrimidine-4-yl)-2,6-dimethyl-4-oxo-4H-pyran-3-carboxamide 4.52 g (Yield: 74%) of the title compound was obtained in a similar way to the method described in Example 27, except that N-(2,6-dimethoxypyrimidine-4-yl)-3-oxo-butyramide (m.p. 107°-109° C.) was used as raw material.

m.p.: 202°-203.5° C.

I.R. (KBr disc): $\nu c=0$ 1653, 1700 cm$^{-1}$.

NMR δvalue (CDCl$_3$): 2.28 (s, 3H), 2.78 (s, 3H), 3.91 (s, 6H), 6.20 (s, 1H), 7.17 (s, 1H), 12.25 (br., 1H).

EXAMPLE 32

N-(2-chlorophenyl)-2,6-dimethyl-4-oxo-4H-pyran-3-carboxamide

The title compound was obtained in a similar way to the method described in Example 26, except that N-methylpiperidine was used as tertiary amine. (Yield: 65%)

m.p.: 206°-207° C.

EXAMPLE 33

N-(2-chlorophenyl)-2,6-dimethyl-4-oxo-4H-pyran-3-carboxamide

The title compound was obtained in a similar way to the method described in Example 26, except that N,N-dimethylcyclohexylamine was used as tertiary amine. (Yield 61%).

m.p. 206°-207° C.

EXAMPLE 34

N-(2-chlorophenyl)-2,6-dimethyl-4-oxo-4H-pyran-3-carboxamide

The title compound was obtained in a similar way to the method described in Example 26, except that N,N,N',N'-tetramethyl-1,3-propanediamine was used as tertiary amine. (Yield: 71%)

m.p. 206°-207° C.

EXAMPLE 35

N-(2-chlorophenyl)-2,6-dimethyl-4-oxo-4H-pyran-b 3-carboxamide

A solution of 4.23 g (20 m mol) of o-chloroacetoacetanilide, 3.11 g (40 m mol) of 40% aqueous solution of methylamine and 20 ml of toluene, after adding one drop of acetic acid, stirred for 8 hours at room temperature and was heated to distill off the resulted water together with about 10 ml of toluene. After 8.10 g (80 m mol) of triethylamine was added, a solution of 7.10 g (50 m mol) of 2,2,6-trimethyl-4H-1,3-dioxin-4-one in 18 ml of toluene was dropwise added over a period of 40 minutes while the reaction mixture was refluxing, and was further refluxed for 3 hours. The reaction mixture was cooled to room temperature after distilling off about 12 ml of solvent. The resulting crystals were filtered, washed and dried under reduced pressure to obtain 3.39 g (Yield 61%) of the title compound.

m.p.: 206°-207° C.

EXAMPLE 36

N-(2-chlorophenyl)-2,6-dimethyl-4-oxo-4H-pyran-3-carboxamide

A mixture of 4.23 g (20 m mol) of o-chloroacetoacetanilide, 2.55 g (20 m mol) of o-chloroaniline and 20 ml of toluene, after adding one drop of hydrochloric acid was refluxed for 2 hours while the resulted water was distilled off from the reaction system together with about 10 ml of toluene. After 9.30 g (80 m mol) of N,N,N',N'-tetramethylethylenediamine was added to the remaining solution, a solution of 9.94 g (70 m mol) of 2,2,6-trimethyl-4H-1,3-dioxin-4-one in 25 ml of toluene was dropwise added over a period of 15 minutes.

The reaction mixture was further refluxed for 2 hours and then cooled to room temperature. The resulting crystals were filtered, washed and dried under reduced pressure to obtain 3.43 g of the title compound. (Yield: 62%)

m.p. 206°–207° C.

EXAMPLE 37

N-(2-chlorophenyl)-2,6-dimethyl-4-oxo-4H-pyran-3-carboxamide

A solution of 4.23 g (20 m mol) of o-chloroacetoacetanilide, 1.46 g (20 m mol) of n-butylamine and 20 ml of toluene, after one drop of acetic acid was added, was stirred for 1.5 hours at 60° C. and was refluxed for 30 minutes while resulted water was distilled off from the reaction mixture together with about 10 ml of toluene. After 8.10 g (80 m mol) of triethylamine was added, a solution of 4.20 g (50 m mol) of diketene in 20 ml of toluene was dropwise added over a period of 40 minutes and the reaction mixture was further refluxed for 2 hours. The reaction mixture was heated to distill off about 12 ml of solvent from the reaction mixture and was cooled to room temperature. The resulting crystals were filtered off, washed and dried under reduced pressure to obtain 1.59 g of the title compound. (Yield: 29%).

m.p.: 206°–207° C.

EXAMPLE 38

2-Ethyl-6-methyl-4-oxo-N-phenyl-4H-pyran-3-carboxamide.

The title compound was prepared from 3-oxo-N-phenylvaleramide (m.p. 84.0°–85.5° C.) as raw material in a similar way to the method described in Example 27. (Yield: 59%)

What we claim is:

1. A process for preparing a pyrone-3-carboxamide compound, which comprises reacting a compound of the formula (I) or (I'):

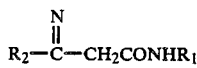

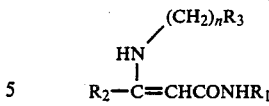

wherein $R_1$ is an aryl group; a 5- or 6-member heterocyclic group having from 1 to 3 hetero atoms selected from the group consisting of nitrogen, sulfur and oxygen; or an aryl group or 5- or 6-member heterocyclic group having from 1 to 3 hetero atoms selected from the group consisting of nitrogen, sulfur and oxygen, and substituted by halogen, alkyl, alkoxy, alkoxycarbonyl, cyano, nitro or trifluoromethyl;

$R_2$ is a $C_{1-11}$ alkyl; lower alkenyl; lower alkynyl; cycloalkyl; lower alkoxyalkyl; phenyl; aralkyl; aralkyl substituted by halogen, lower alkyl or lower alkoxy; halogenated alkyl; a 5- or 6-member heterocyclic group having 1 to 3 hetero atoms selected from the group consisting of nitrogen, sulfur and oxygen; or a 5- or 6-member heterocyclic group having 1 to 3 hetero atoms selected from the group consisting of nitrogen, sulfur and oxygen, substituted by halogen, alkyl or phenyl;

$R_3$ is a dialkylamino, cycloalkylamino or heterocyclic amino group selected from the group consisting of pyrrolidino, piperidino, piperazino and morpholino; and n is an integer from 0–6;

with a compound of formula (II):

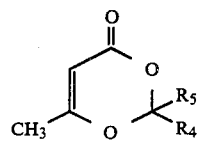

wherein each of $R_4$ and $R_5$ is hydrogen, alkyl, or phenyl, or $R_4$ and $R_5$ together with the carbon atom to which they are bonded form a cycloalkyl group.

2. The process of claim 1, in which $R_3(CH_2)_n$— is N,N-dimethylamino.

3. The process of claim 1, in which n is 2 and $R_3$ is dimethylamino or 1-pyrrolidinyl.

4. The process of claim 1, in which the compound of formula (II) is a diketene-acetone adduct, a diketene-methylethylketone adduct or a diketene-methylisobutylketone adduct.

5. The process of claim 1, in which the compound of formula (II) is reacted in an amount of 1.5–3.0 moles per mole of the compound of formula (I) or (I').

6. The process of claim 1, in which the reaction is carried out in an aromatic hydrocarbon solvent.

7. The process of claim 6, in which the reaction is carried out while distilling off a part of the solvent.

* * * * *